United States Patent [19]
Kadoya

[11] Patent Number: 5,937,266
[45] Date of Patent: Aug. 10, 1999

[54] LIGHT IRRADIATING DEVICE EMPLOYING LIGHT IRRADIATING MODULES EQUIPPED WITH A CLEANING MECHANISM

[75] Inventor: Masahiro Kadoya, Hachioji, Japan

[73] Assignee: Photoscience Japan Corporation, Japan

[21] Appl. No.: 08/677,962

[22] Filed: Jul. 10, 1996

Related U.S. Application Data

[63] Continuation-in-part of application No. 08/613,041, Mar. 8, 1996, Pat. No. 5,792,433.

[51] Int. Cl.⁶ ....................................................... C02F 1/32
[52] U.S. Cl. ............................................................ 422/186.3
[58] Field of Search .................................... 422/186.3, 24

[56] References Cited

U.S. PATENT DOCUMENTS

| | | | |
|---|---|---|---|
| 3,182,193 | 5/1965 | Ellner et al. | 250/43.5 |
| 3,562,520 | 2/1971 | Hippen | 250/43 |
| 4,367,410 | 1/1983 | Wood | 250/431 |
| 5,133,945 | 7/1992 | Hallett | 422/186.3 |
| 5,227,140 | 7/1993 | Hager et al. | 422/186.3 |
| 5,266,280 | 11/1993 | Hallett | 422/186.3 |
| 5,401,474 | 3/1995 | Hager et al. | 422/186.3 |
| 5,418,370 | 5/1995 | Maarschalkerweerd | 250/431 |
| 5,501,843 | 3/1996 | Peterson | 422/186.3 |

*Primary Examiner*—Daniel J. Jenkins
*Attorney, Agent, or Firm*—Graham & James LLP

[57] ABSTRACT

The efficiency of liquid light irradiation treatments is improved by making it possible to perform continuous liquid light irradiation treatments without lowering the purity of the treated liquid and without any need for interrupting the light irradiation treatment or disassembling the device. This is accomplished by stripping away contaminants adhering to all of the light-transmitting tubes of light irradiating modules (which make up the light irradiating device) during the light irradiation treatment of the liquid in question. The present invention provides a light irradiating device in which [a] light irradiating modules in which a plurality of light-transmitting tubes containing light irradiating lamps are attached to a frame are mounted inside a housing as detachable integral units so that flow paths for the light irradiation treatment of a fluid are formed, [b] a moving body is attached to a moving means which is installed inside the upper portion of the aforementioned housing, [c] supporting bodies for cleaning parts are detachably connected to the aforementioned moving body, and these supporting bodies are positioned in close proximity to the outside surfaces of the aforementioned light-transmitting tubes, and [d] cleaning parts which slide along the outside surfaces of the aforementioned light-transmitting tubes are detachably mounted on the aforementioned supporting bodies so that contaminants adhering to the aforementioned light-transmitting tubes are stripped away in the presence of the liquid during the light irradiation treatment of said liquid.

11 Claims, 4 Drawing Sheets

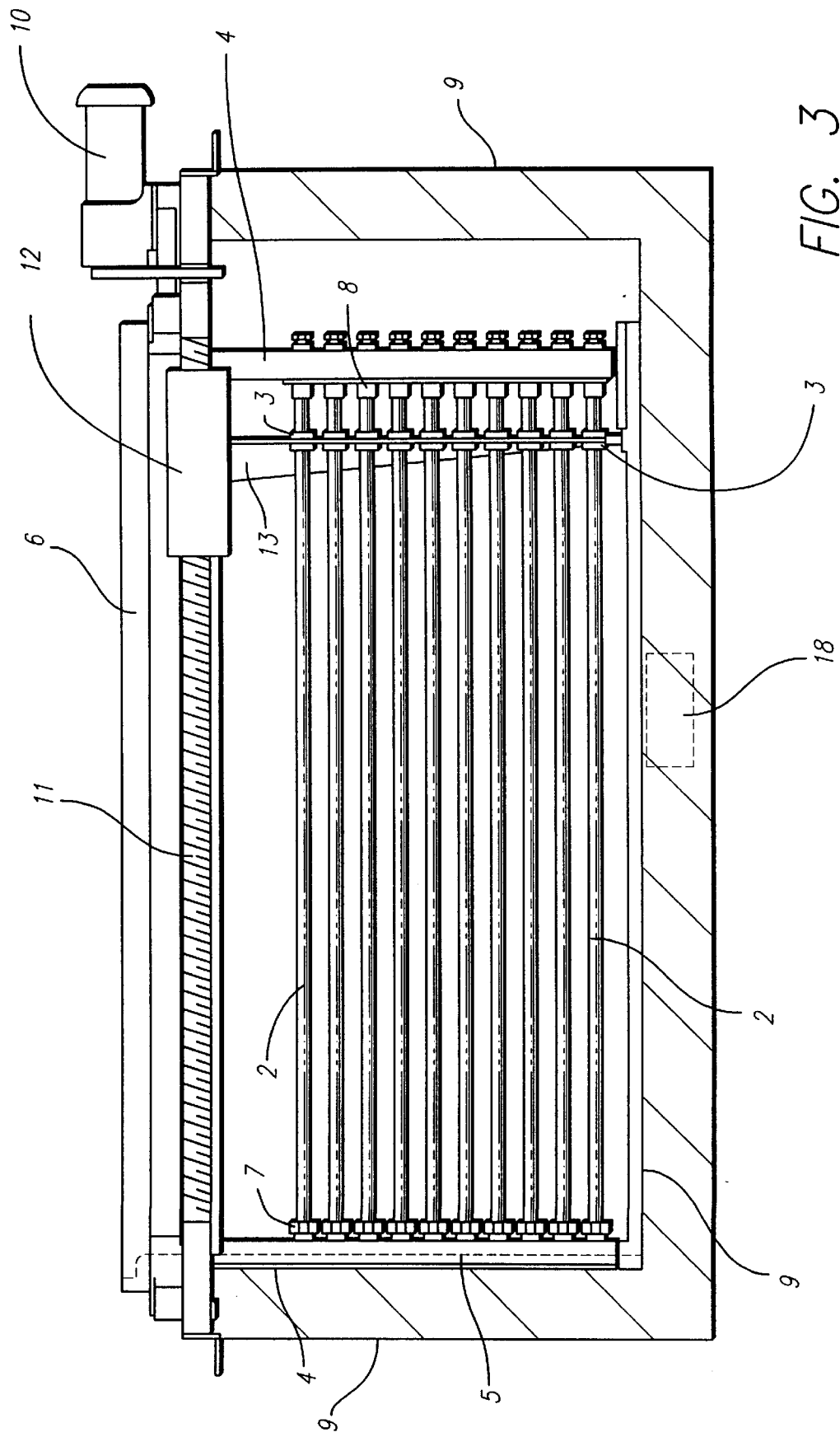

LIGHT IRRADIATING DEVICE EMPLOYING LIGHT IRRADIATING MODULES EQUIPPED WITH A CLEANING MECHANISM

RELATED APPLICATION INFORMATION

The present application is a continuation-in-part of application Ser. No. 08/613,041 filed Mar. 8, 1996, now U.S. Pat. No. 5,792,433.

BACKGROUND OF THE INVENTION

1. Field of the Invention

The present invention concerns light irradiating devices which produce treated liquids that are free of bacteria, organic matter or harmful substances, etc., by performing a light irradiation treatment such as eradication of bacteria, oxidative decomposition of organic matter or decomposition of harmful substances, etc., in said liquids.

2. Background of the Prior Art and Related Information

In conventional light irradiating devices, light-transmitting tubes containing (e.g.) ultraviolet lamps as light irradiating lamps are installed one by one at intervals inside a housing, and a liquid containing bacteria, organic matter or harmful substances, etc., which is caused to flow into said housing is subjected to an ultraviolet irradiation treatment, thus causing eradication of the aforementioned bacteria, oxidative decomposition of the aforementioned organic matter or decomposition of the aforementioned harmful substances, etc., so that a treated liquid which is free of said bacteria, organic matter or harmful substances, etc., is obtained. Such treated liquids can then be used in various industrial fields.

However, in the case of such conventional ultraviolet irradiating devices, contaminants such as organic matter, etc., present in the liquid being subjected to the ultraviolet irradiation treatment adhere to the outside surfaces of the light-transmitting tubes containing the aforementioned ultraviolet lamps during said treatment; this adhesion of contaminants leads to problems such as a drop in the purity of the treated liquid and a drop in the ultraviolet irradiation efficiency, etc.

Accordingly, in conventional ultraviolet irradiating devices, the following type of cleaning operation is necessary: the ultraviolet irradiation treatment is interrupted (and in some cases, the ultraviolet irradiating device is disassembled), and the light-transmitting tubes with adhering contaminants are removed one by one and cleaned by hand; then, after this cleaning is completed, the light-transmitting tubes are re-attached to the ultraviolet irradiating device one by one. As a result, this cleaning operation requires considerable time and expense, leading to a drop in the efficiency of the ultraviolet irradiation treatment.

Conventional ultraviolet irradiating devices also include devices in which frames to which a plurality of light-transmitting tubes containing ultraviolet lamps are attached are installed inside a housing. However, in devices of this type, no mechanism for cleaning ultraviolet light-transmitting tubes with adhering contaminants is provided; instead, it is necessary to perform a cleaning operation in which the frames are removed from the device and the light-transmitting tubes attached to the respective frames are manually cleaned one by one, after which the frames with attached light-transmitting tubes are re-attached to the device following the completion of cleaning. Thus, such devices are the same as other conventional devices in terms of suffering from the aforementioned drawbacks.

Furthermore, in cases where it is necessary to replace ultraviolet lamps which have burned out or become damaged during the ultraviolet irradiation treatment of a liquid, such replacement is commonly accomplished by disassembling the device, removing the ultraviolet lamps one by one and replacing said lamps by hand. No operation in which ultraviolet irradiating modules consisting of light-transmitting tubes containing ultraviolet lamps are removed from the device as freely detachable integral units (so that the aforementioned burned-out or damage ultraviolet lamps can be simply replaced) is performed. Accordingly, such devices still suffer from the aforementioned drawback in terms of ultraviolet lamp replacement.

Furthermore, ultraviolet irradiating devices which have been used experimentally include devices in which [a] a cleaning body to which a brush, etc., is attached is fit over a screw shaft installed inside a device containing a single ultraviolet lamp equipped with a light-transmitting tube (with said cleaning body being installed so that screw type motion of said cleaning body is possible), and [b] the aforementioned cleaning body is caused to perform a reciprocating motion along the outside surface of the aforementioned light-transmitting tube by causing the aforementioned screw shaft to rotate, thus causing contaminants adhering to said light-transmitting tube to be stripped away so that said light-transmitting tube is cleaned.

However, such conventional ultraviolet irradiating devices with a cleaning mechanism which uses a cleaning body are devices in which a single ultraviolet lamp equipped with a light-transmitting tube is installed inside the device. Such devices have not included devices in which a plurality of ultraviolet lamps equipped with light-transmitting tubes are simultaneously and automatically cleaned. Furthermore, in such conventional ultraviolet irradiating devices, the screw shaft attached to the light-transmitting tube and the cleaning body with an attached brush, etc., are formed as an integral unit. Accordingly, in cases where a burned-out or damaged ultraviolet lamp is to be replaced, it is necessary to disassemble the screw shaft and cleaning body (with attached brush, etc.), and then to remove the ultraviolet lamp from the housing so that said lamp can be replaced. Thus, an extremely laborious operation is required, so that the treatment efficiency is poor.

SUMMARY OF THE INVENTION

The present invention ameliorates the drawbacks of the aforementioned conventional irradiating devices. One object of the present invention is to improve the efficiency of liquid light irradiation treatments by making it possible to perform continuous light irradiation treatments of liquids without lowering the purity of the treated liquid and without any need for interrupting the light irradiation treatment or disassembling the device. This is accomplished by stripping away contaminants adhering to the light-transmitting tubes of light irradiating modules (which make up the light irradiating device) during the light irradiation treatment of the liquid in question, instead of individually removing light-transmitting tubes with adhering contaminants and stripping away said contaminants.

Furthermore, another object of the present invention is to simplify and facilitate separation of the cleaning parts and moving body by attaching cleaning parts in a freely detachable manner to a moving body such as a screw nut, etc. (including guides and supporters), which is installed on a moving means such as a screw shaft, etc., and to reduce the cost of manufacture, repair and inspection, etc., of the light irradiating device by allowing the removal of light irradiating modules consisting of a plurality of light-transmitting tubes (containing light irradiating lamps) as freely detachable integral units from the housing, as well as the re-installation of said modules in the housing, in a short time by means of a one-touch operation.

Furthermore, still another object of the present invention is to allow a lamp replacement process which is such that in cases where burned-out or damaged light irradiating lamps among the plurality of lamps in light-transmitting tubes making up the respective light irradiating modules are to be replaced, light irradiating modules comprising a plurality of light-transmitting tubes containing light irradiating lamps are simply removed from the housing as freely detachable integral units so that the aforementioned burned-out or damaged light irradiating lamps can be quickly and easily removed from the frame and replaced (instead of being removed from the device one by one and replaced). A particular object of the present invention is to allow the quick and easy replacement of light irradiating lamps in cases where said light irradiating lamps are detachably connected to connectors installed on the aforementioned frame.

The present invention is directed to a light irradiating device comprising light irradiating modules equipped with a cleaning mechanism. The device of the present invention is characterized by the fact that [a] light irradiating modules in which a plurality of light-transmitting tubes containing light irradiating lamps are attached to a frame are mounted inside a housing as detachable integral units so that flow paths for the light irradiation treatment of a fluid are formed, [b] a moving body such as a screw nut, etc., is attached to a moving means such as a screw shaft, etc., which is installed inside the aforementioned housing, [c] the tip ends of the aforementioned moving body are positioned in close proximity to the outside surfaces of the aforementioned light-transmitting tubes, and [d] cleaning parts are detachably mounted on the tip ends of the aforementioned moving body so that contaminants adhering to the aforementioned light-transmitting tubes are stripped away during the light irradiation treatment of the fluid in question.

Furthermore, the present invention is also characterized by the fact that in the aforementioned light irradiating device comprising light irradiating modules equipped with a cleaning mechanism, a plurality of light-transmitting tubes containing light irradiating lamps are detachably connected (in a water-tight state) to respective connectors installed at intervals on the aforementioned frame, so that the light irradiating lamps can be quickly and easily detached from the aforementioned frame, and so that the deterioration of electrical lead wires caused by light irradiation can be prevented.

Furthermore, the present invention is also characterized by the fact that in the aforementioned light irradiating device comprising light irradiating modules equipped with a cleaning device, [a] light irradiating lamps are installed inside light-transmitting tubes which are closed at one end and open at the other end, [b] the open end portions of the aforementioned light-transmitting tubes are detachably connected to respective connectors installed at intervals on the aforementioned frame, and [c] the closed end portions of the aforementioned light-transmitting tubes are attached to detachable retaining parts installed at intervals on the aforementioned frame, so that the light irradiating lamps can be detached from the aforementioned frame even more quickly and easily.

Furthermore, the present invention is also characterized by the fact that in the aforementioned light irradiating device comprising light irradiating modules equipped with a cleaning device, [a] a plurality of light irradiating modules constituting detachable integral units are installed parallel to each other at intervals inside the aforementioned housing, [b] a moving body such as a screw nut, etc., is attached to a moving means such as a screw shaft, etc., which is installed in the aforementioned housing, [c] supporting bodies to which cleaning parts are attached are installed on the aforementioned moving body, [d] said supporting bodies are positioned in close proximity to the outside surfaces of all of the light-transmitting tubes of the aforementioned light irradiating modules, and [e] cleaning parts such as scrapers or brushes, etc., which slide along the outside surfaces of the aforementioned light-transmitting tubes are attached (in a freely detachable manner) to the aforementioned supporting bodies, so that contaminants adhering to the outside surfaces of all of the light-transmitting tubes of the light irradiating modules are simultaneously stripped away during the light irradiation treatment of the aforementioned liquid.

Furthermore, the present invention is also characterized by the fact that in the aforementioned light irradiating device comprising light irradiating modules equipped with a cleaning device, a driving means such as a motor, etc., is connected to the aforementioned moving means such as a screw shaft, etc., so that the supporting bodies to which the aforementioned scrapers or brushes that slide along the outside surfaces of the aforementioned light-transmitting tubes are attached are caused to move in a linked motion, thus causing contaminants adhering to the outside surfaces of the plurality of light-transmitting tubes in each light irradiating module to be automatically stripped away. Moreover, the present invention is also characterized by the fact that if necessary, a light irradiation monitor which monitors the amount of irradiation of the aforementioned light irradiating lamps and the light transmissivity of the aforementioned liquid is installed inside the aforementioned housing of the light irradiating device, thus promoting the automation of the aforementioned stripping away of contaminants from the plurality of light-transmitting tubes in each light irradiating module.

BRIEF DESCRIPTION OF THE DRAWINGS

FIG. 3 is a sectional view of an ultraviolet irradiating device in which ultraviolet irradiating modules (equipped with scrapers) of the present invention are installed in multiple rows as detachable integral units.

DETAILED DESCRIPTION OF THE INVENTION

When a liquid is subjected to a continuous ultraviolet irradiation treatment, organic matter and other contaminants present in the liquid adhere to the outside surfaces of the plurality of light-transmitting tubes in each light irradiating module, so that the amount of light irradiation drops. Accordingly, the present invention provides moving means, such as a screw shaft, etc., which is actuated during the light irradiation treatment of the liquid so that supporting bodies are caused to move, thus causing cleaning parts (scrapers or the like) attached to said supporting bodies to slide along the outside surfaces of the respective light-transmitting tubes of each light irradiating module. As a result, contaminants adhering to the outside surfaces of the respective light-transmitting tubes are stripped and cleaned away in the presence of the liquid. Accordingly, it is possible to subject the liquid to a continuous ultraviolet irradiation treatment while preventing any substantial drop in the amount of light irradiation of the light irradiating lamps that might be caused by the adhesion of contaminants to the light-transmitting tubes in each light irradiating module.

Furthermore, the cleaning parts and the moving body (including guides and supporters) installed on the moving means are connected in a detachable manner so that the separation of said cleaning parts and moving body is simplified and facilitated. This allows the light irradiating modules to be removed from the housing or mounted in the housing as detachable integral units by means of a quick one-touch operation. Moreover, in regard to the replacement of burned-out or damaged ultraviolet lamps as well, the light irradiating lamps need not be removed and replaced one by one; instead, the light irradiating modules are simply removed from the housing as detachable integral units, so that the aforementioned burned-out or damaged light irradiating lamps can be quickly and easily removed from the frame and replaced.

Figure 1:
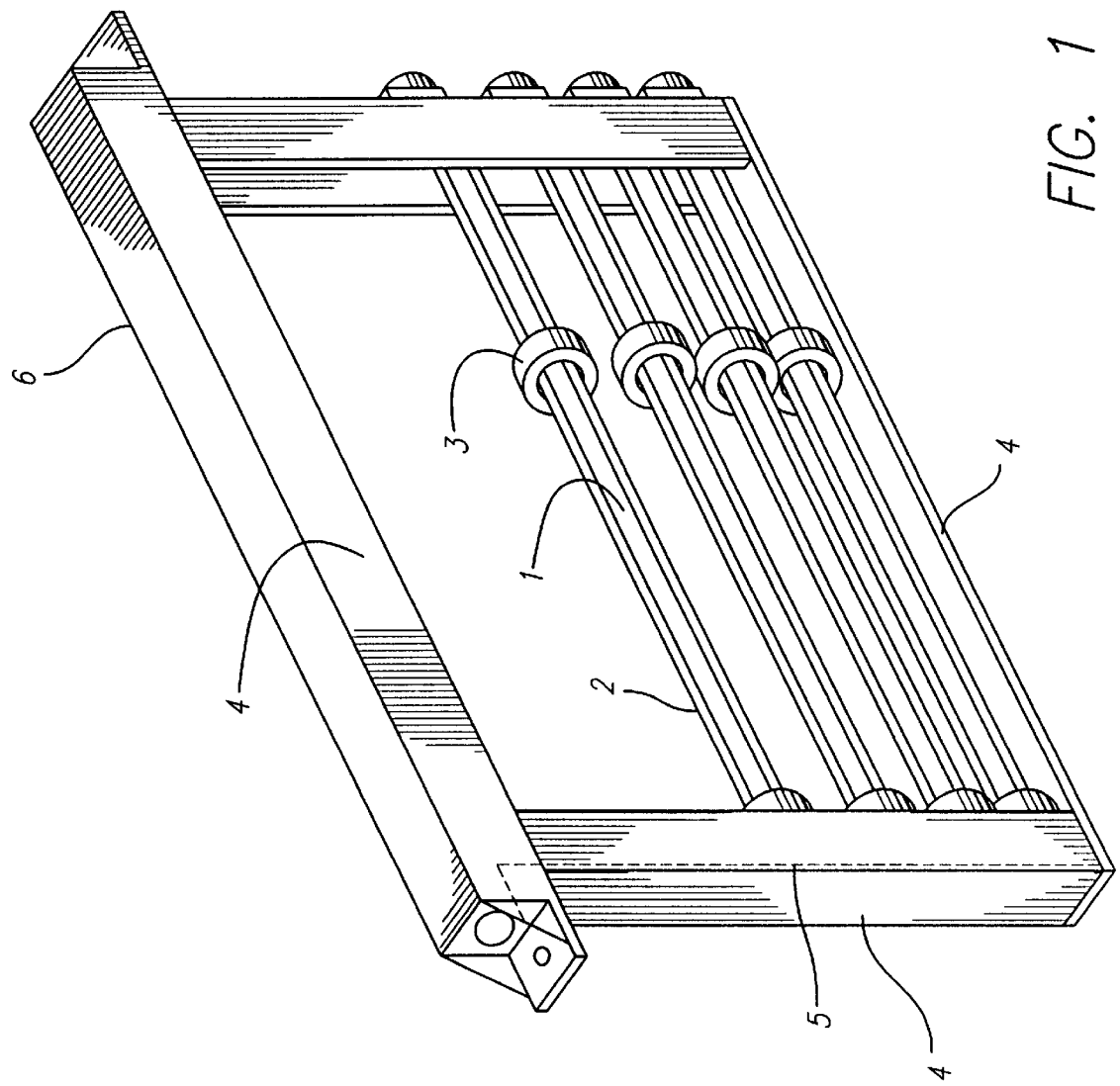
FIG. 1 is a perspective view of an ultraviolet irradiating module equipped with scrapers constructed according to the present invention.

In a preferred embodiment, the light irradiating device employing light irradiating modules equipped with a cleaning mechanism provided by the present invention may be described as follows: i.e., as is shown in FIG. 1, scrapers 3 which slide along the outside surfaces of light-transmitting tubes 2 containing ultraviolet lamps 1 (as light irradiating lamps) are fit over the outside surfaces of said light-transmitting tubes 2. A plurality of these light-transmitting tubes 2 are attached in a fence-form configuration to a C-shaped hollow frame 4 made of stainless steel. Specifically, said light-transmitting tubes are attached to said frame 4 in a water-tight manner one above the other, with spaces left between the individual light-transmitting tubes 2. Furthermore, electrical lead wires 5 which run through the hollow frame 4 are connected to the ultraviolet lamps 1, thus forming an ultraviolet irradiating module 6.

The lamps used as the aforementioned ultraviolet lamps 1 may be low-pressure ultraviolet lamps with a principal wavelength of 254 nm, low-pressure ultraviolet lamps with principal wavelengths of 185 nm and 254 nm, or medium- to high-pressure ultraviolet lamps with principal wavelengths of 185 nm, 254 nm and 365 nm. Furthermore, depending on the ultraviolet reaction treatment used, various other types of lamps emitting wavelengths of 700 nm or less, e.g., solar ultraviolet lamps, chemical lamps, black light lamps, metal halide lamps or sodium lamps, etc., may be used as ultraviolet irradiating lamps.

In regard to the material of the light-transmitting tubes 2 which contain the ultraviolet lamps 1, tubes consisting of a material which has a high ultraviolet transmissivity, e.g., quartz glass or Teflon, etc., are used. Furthermore, light-transmitting tubes 2 which are open at both ends are used, and both ends of these light-transmitting tubes 2 are attached to the frame 4 in a detachable, water-tight manner.

In addition to the aforementioned stainless steel, the material used for the frame 4 may be some other material such as a ceramic or plastic, etc., which has physical strength and which does not elute impurities. Furthermore, besides the aforementioned "C" shape, the frame 4 may have a square shape or any other desired shape, as long as said shape is capable of maintaining the physical strength of the frame 4.

Figure 2:
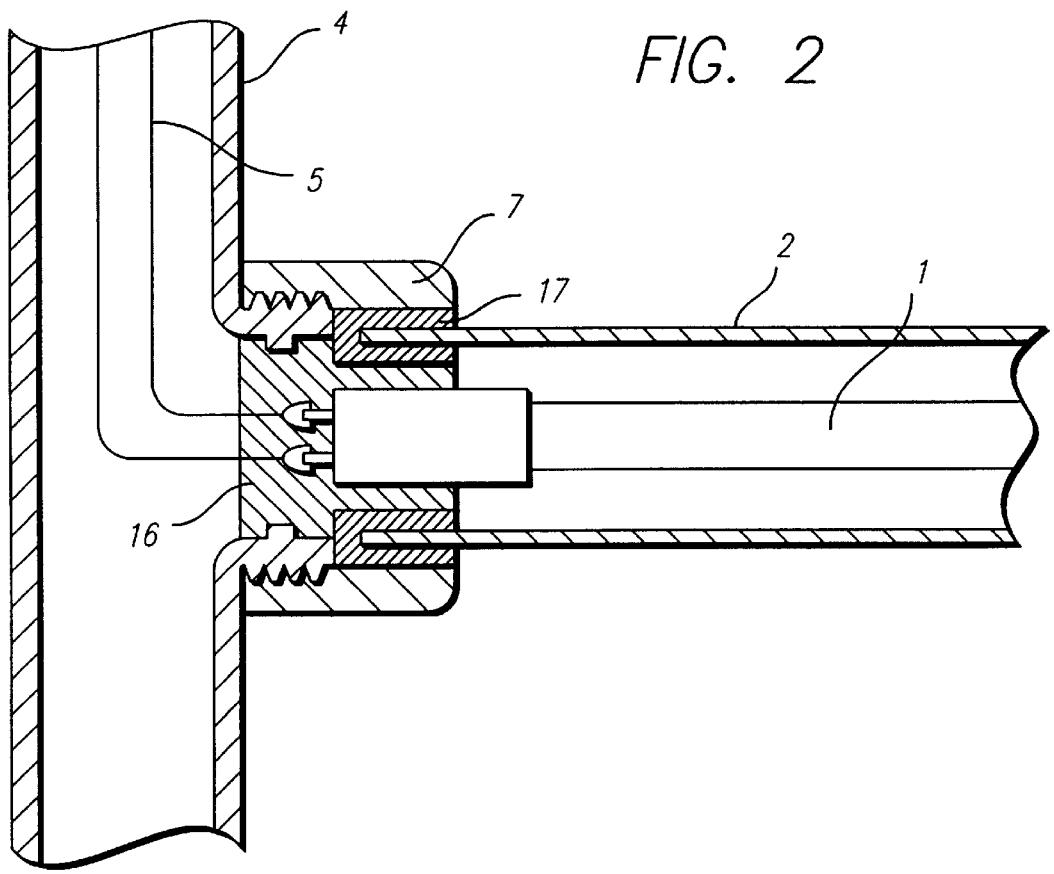
FIG. 2 is an enlarged sectional view which shows the ultraviolet light-transmitting tubes containing ultraviolet irradiating lamps attached to the frame in the present invention.

Furthermore, as is shown in FIG. 2, the frame 4 is formed as a hollow part, and electrical lead wires 5 which are connected to the ultraviolet lamps 1 are run through the hollow interior of the frame 4. When these electrical lead wires 5 are connected to the ultraviolet lamps 1 inside the light-transmitting tubes 2 which are attached (in a detachable manner) to connectors 7 installed on the frame 4, the accommodation of said electrical lead wires 5 is good; furthermore, there is no damage to the electrical lead wires 5 when the ultraviolet irradiating module 6 is attached to or detached from the housing 9, and no deterioration of the coverings of the electrical lead wires 5 due to ultraviolet irradiation.

Furthermore, in order to insure stable and reliable attachment of the light-transmitting tubes 2 (containing the ultraviolet lamps 1) to the frame 4 of the ultraviolet irradiating module 6, the end portions of said light-transmitting tubes 2 are attached in a water-tight detachable manner (via packing 17) to holders 16 for the aforementioned connectors 7 which are installed at intervals on the frame 4 as shown in FIG. 2. Accordingly, the ultraviolet lamps 1 can always be easily inserted into the centers of the light-transmitting tubes 2; furthermore, the ultraviolet lamps 1 can be quickly and easily detached from the frame 4.

Moreover, if the light-transmitting tubes 2 containing the ultraviolet lamps 1 are closed at one end, and the closed end portions of these light-transmitting tubes 2 are attached to the frame 4 via detachable retaining parts 8, the closed end portions of the light-transmitting tubes 2 can be stably fastened to the frame 4, and the light-transmitting tubes 2 can easily be removed from the frame 4 by removing the detachable retaining parts 8.

Furthermore, as is shown in FIG. 3, the aforementioned ultraviolet irradiating module 6 is installed in a detachable manner inside a housing 9 into which a liquid containing bacteria, organic matter or harmful substances, etc., is caused to flow, so that flow paths for performing an ultraviolet irradiation treatment (such as eradication of bacteria, oxidative decomposition of organic matter or decomposition of harmful substances, etc.) are formed. In some cases, a single such ultraviolet irradiating module 6 may be installed inside the housing 9 as an integral unit; in other cases (depending on the treatment flow rate), a plurality of these modules 6 may be installed parallel to each other at intervals in a multi-row configuration.

Figure 4:
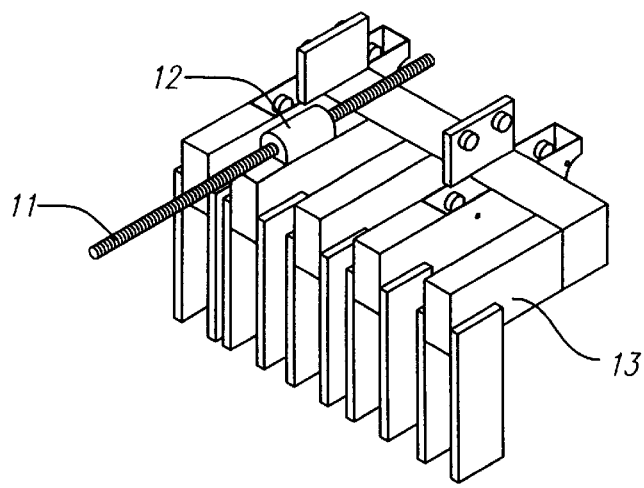
FIG. 4 is a perspective view which illustrates the screw shaft and the moving body attached to the screw nut in the ultraviolet irradiating device of the present invention.

Furthermore, a moving means such as a screw shaft 11, etc., which is connected to a motor 10 is installed as a moving mechanism inside the upper portion of the housing 9 (in a position which is such that said moving means does not contact the liquid). As is shown in FIG. 4, a moving body such as a screw nut 12, etc., is screwed onto the screw shaft 11; this screw nut 12 is caused to move by the rotation of the screw shaft 11.

Besides the aforementioned screw shaft 11 connected to a motor 10, it would also be possible to use a moving plate (which is installed so that said plate can be caused to slide along a fixed shaft by a rope connected to the aforementioned motor 10) as the aforementioned moving mechanism. Furthermore, any other desired type of mechanism may be used, as long as said mechanism is capable of causing the aforementioned moving body to move.

Figure 5:
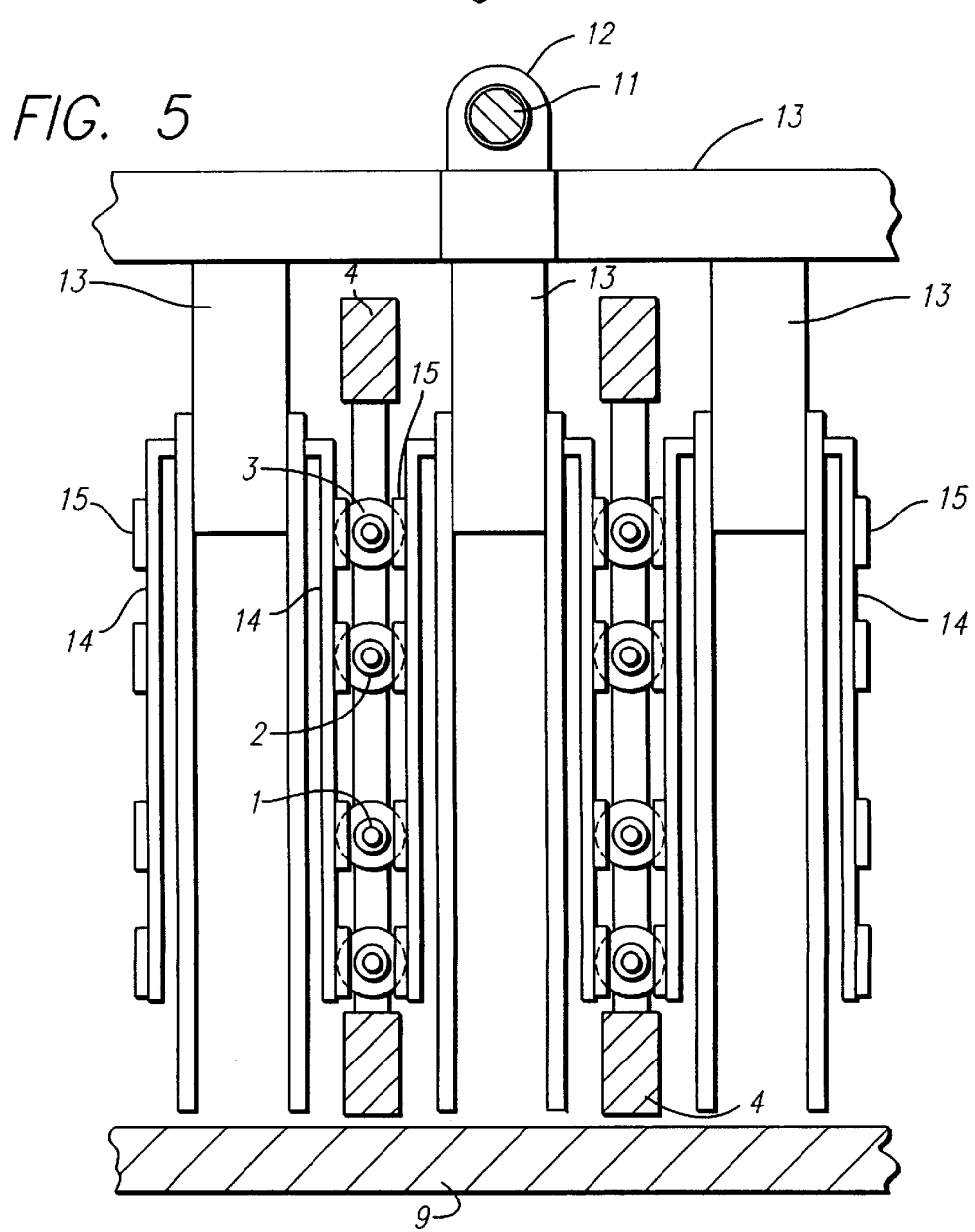
FIG. 5 is a sectional view which illustrates the detachable mounting of scrapers (fit over the light-transmitting tubes of the ultraviolet irradiating modules) by means of supporters fastened to guides which are installed on the moving body (forming an integral part of the screw nut) in the present invention.

A moving body 13 which moves as a unit with the screw nut 12 is attached to the screw nut 12, and cleaning parts such as scrapers 3, etc., are attached (in a detachable manner) to the side surfaces of the lower portions of this moving body 13. As is shown in FIG. 5, guides 14 may be detachably mounted on the side surfaces of the lower portions of the moving body 13 as supporting parts for the aforementioned cleaning parts such as scrapers 3, etc., and supporters 15 to which the scrapers 3 are attached may be installed on the guides 14.

Figure 6:
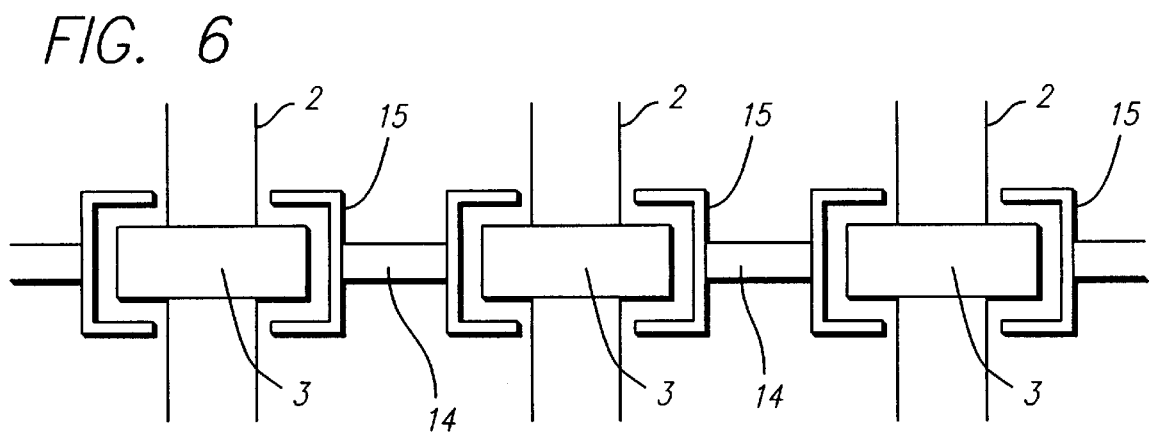
FIG. 6 is a plan view which illustrates the detachable mounting of scrapers (fit over the light-transmitting tubes of the ultraviolet irradiating modules) by means of supporters fastened to guides which are installed on the moving body in the present invention.

Furthermore, the guides 14 on which the aforementioned supporters 15 are installed are positioned in close proximity to the outside surfaces of the aforementioned light-transmitting tubes 2; moreover, as is shown in FIG. 6, the scrapers 3 are detachably held between C-shaped supporters 15, so that the scrapers 3 slide along the outside surfaces of the light-transmitting tubes 2 together with the movement of the supporters 15.

Furthermore, the system is constructed so that the supporters 15 can be withdrawn from the scrapers 3 by lifting the guides 14 (or guides 14 and moving body 13) upward.

The structure which is used for the detachable mounting of the scrapers 3 by means of the aforementioned supporters 15 may be a structure other than that described above, as long as said structure allows the supporters 15 to be withdrawn from the scrapers 3 by lifting the guides 14 (or guides 14 and moving body 13) upward.

The material used for the scrapers 3 may be natural rubber, synthetic rubber or Teflon, etc. Furthermore, a cleaning cloth (for example, a cleaning cloth manufactured by Toray K.K.) may be bonded to the inside surfaces of said scrapers 3. Moreover, besides scrapers 3, it would also be possible to other cleaning parts (such as brushes or bristles, etc.), as long as said cleaning parts are capable of stripping away contaminants.

Besides the comb-form moving body 13 shown in FIG. 5, the moving body 13 with attached cleaning parts may also be an inverted U-form body, a rod-form body or a plate-form body. The moving body 13 and the guides 14 may be formed as an integral unit, or may be formed as separable parts.

The operation of the device of the present invention may be described as follows: first, a liquid containing bacteria, organic matter or harmful substances, etc., is caused to flow into the flow paths inside the housing 9, and this liquid is irradiated with ultraviolet light from the ultraviolet lamps 1 contained in the light-transmitting tubes 2 so that an ultraviolet irradiation treatment (such as the eradication of bacteria, oxidative decomposition of organic matter or decomposition of harmful substances, etc.) is performed in said liquid. Then, the treated liquid, which is free of bacteria, organic matter or harmful substances, etc., is caused to flow out of the housing 9, and is stored.

As the ultraviolet irradiation treatment of the aforementioned liquid is continued, contaminants such as organic matter, etc., present in the liquid adhere to the outside surfaces of the light-transmitting tubes 2, so that the amount of ultraviolet irradiation drops. Accordingly, during the ultraviolet irradiation treatment of the liquid, the motor 10 is continuously or intermittently driven so that the screw shaft 11 is caused to rotate in the forward and reverse directions, thus causing the screw nut 12 to perform a reciprocating motion along the screw shaft 11.

The moving body 13 on which the guides 14 with attached supporters 15 are installed performs a reciprocating motion together with the screw nut 12; accordingly, the scrapers 3 perform a reciprocating motion while rubbing against the outside surfaces of the light-transmitting tubes 2, so that organic matter and other contaminants adhering to the outside surfaces of the light-transmitting tubes 2 are stripped away in the presence of the liquid, thus causing the light-transmitting tubes 2 to be cleaned.

As was described above, the cleaning of contaminants from the light-transmitting tubes 2 by means of the aforementioned scrapers 3 may be performed while the ultraviolet irradiation treatment is being performed. In some cases, however, this cleaning operation may be performed after it has been confirmed that the amount of ultraviolet irradiation from the ultraviolet lamps 1 has dropped due to the adhesion of contaminants to the light-transmitting tubes 2.

For example, it would be possible to use a system in which an ultraviolet irradiation monitor 18 which monitors the amount of irradiation from the ultraviolet lamps 1 and the ultraviolet light transmissivity of the liquid is installed inside the housing 9, so that the cleaning operation of the light-transmitting tubes 2 is initiated when a drop in the amount of irradiation from the ultraviolet lamps 1 or a drop in the ultraviolet light transmissivity of the liquid is confirmed, and so that this cleaning operation is stopped when an increase in the amount of irradiation from the ultraviolet lamps 1 or an increase in the ultraviolet light transmissivity of the liquid is confirmed. In this way, the aforementioned cleaning operation of the light-transmitting tubes 2 can also be automated.

Furthermore, although this is not shown in the figures, it would also be possible to automate the aforementioned cleaning operation of the light-transmitting tubes 2 using a system in which [a] a detection part (detected by a sensor) which rotates as a unit with the screw shaft 11 is installed on the surface of the screw shaft 11 at one end of said screw shaft 11, [b] the number of rotations of this detection part, i.e., the number of rotations of the screw shaft 11, is detected by a sensor, and [c] on-off control of the motor 10 is performed by counting the number of rotations of the screw shaft 11.

The rotational speed of the screw shaft 11, the moving speed of the scrapers 3 and the frequency of repetition of the cleaning operation are appropriately determined in accordance with the ultraviolet irradiation treatment conditions and the degree of contamination of the light-transmitting tubes 2; ordinarily, however, the rotational speed of the screw shaft 11 is 150 to 250 rpm, the moving speed of the scrapers 3 is 20 to 30 cm per minute, and the frequency of repetition of the cleaning operation is 1 to 3 times every 4 hours.

When contaminants are cleaned from the light-transmitting tubes 2 by the scrapers 3, a bubbling treatment, compressed air treatment, water spraying treatment or ultrasonic treatment may be applied in combination with the cleaning operation by installing a bubble generating device, compressed air jet device, water spray or ultrasonic device inside the housing 9, thus accelerating the stripping and cleaning of contaminants from the light-transmitting tubes 2.

In the present invention, contaminants adhering to the outside surfaces of all of the light-transmitting tubes of the light irradiating modules making up the light irradiating device are simultaneously stripped away from the light-transmitting tubes during the light irradiation treatment of the liquid (instead of the individual light-transmitting tubes being removed and cleaned one by one). Accordingly, the present invention possesses the following superior merits: i.e., the aforementioned liquid can be subjected to a continuous light irradiation treatment without lowering the purity of the treated liquid, and without any need to interrupt the light irradiation treatment of the liquid or disassemble the device; as a result, the efficiency of the light irradiation treatment of the liquid can be increased, and the cost of said treatment can be reduced.

In the present invention, furthermore, the cleaning parts and the moving body (including guides and supporters) are connected in a detachable manner; accordingly, separation of the cleaning parts and moving body can be accomplished quickly and easily. As a result, light irradiation modules consisting of a plurality of light-transmitting tubes containing light irradiating lamps can be quickly removed from the housing (or re-installed in the housing) as detachable integral units by means of a one-touch operation. Thus, the costs of manufacture, repair and inspection, etc., of the light irradiating device can be reduced.

In the present invention, furthermore, burned-out or damaged light irradiating lamps can be replaced by an operation in which the light irradiation modules are simply removed from the housing as detachable integral units, and the aforementioned burned-out or damaged light irradiating lamps are quickly and easily removed from the frame and replaced (instead of an operation in which the light-transmitting tubes containing such burned-out or damaged light irradiating lamps are removed and replaced one by one). Accordingly, the present invention possesses the merit of allowing quick and easy replacement of light irradiating lamps, especially in cases where the light irradiating lamps are detachably connected to connectors installed on the frame.

I claim:

1. A light irradiating device for use with a housing comprising:

a light irradiating module comprising a frame and a plurality of light-transmitting tubes attached to the frame in a water-tight manner, said tubes containing light irradiating lamps and being installed at intervals on the frame, wherein the light irradiating module is adapted to be assembled as a freely detachable integral unit inside the housing so that flow paths used to perform light irradiation treatment of a fluid are formed; and a cleaning mechanism comprising a movable body, moving means for moving the movable body adapted to be installed in a position in the upper portion of the housing, wherein the tip ends of the movable body are positioned in close proximity to the outside surface of the corresponding light-transmitting tube, and a plurality of cleaning parts configured so as to slide along the outside surfaces of the light-transmitting tubes and detachably mounted on the tip ends of the movable body, so that contaminants adhering to the outside surfaces of the light-transmitting tubes are stripped away during the light irradiation treatment of the fluid.

2. A light irradiating device, as defined in claim 1, in which the light irradiating module further comprises a plurality of connectors installed at intervals on the frame, with said plurality of light-transmitting tubes containing light irradiating lamps being attached to respective connectors in a water-tight state and in a freely detachable manner.

3. A light irradiating device, as defined in claim 2, wherein [a] the light-transmitting tubes are closed at one end and open at the other end, [b] the open end portions of said light-transmitting tubes are attached in a water-tight state and in a freely detachable manner to the respective connectors installed at intervals on the frame, and [c] the closed end portions of said light-transmitting tubes are attached to detachable retaining parts which are installed at intervals on the frame.

4. A light irradiating device comprising:

a housing;

a plurality of light irradiating modules installed parallel to each other at intervals inside the housing as detachable integral units; and a cleaning mechanism which is installed in the housing, comprising:

moving means;

a movable body attached to the moving means, and;

a plurality of supporting bodies, including cleaning parts, installed on the movable body, wherein said supporting bodies are positioned in close proximity to the outside surfaces of the light-transmitting tubes of the light irradiating modules.

5. A light irradiating device, as defined in claim 4, further comprising a driving means connected to the moving means.

6. A light irradiating device, as defined in claim 5, further comprising a light irradiation monitor, which monitors the amount of irradiation of the light irradiating lamps and the light transmissivity of the liquid, installed inside the housing.

7. A light irradiating device as defined in claim 1, where the moving means comprises a screw shaft.

8. A light irradiating device as defined in claim 4, wherein the cleaning parts comprise scrapers, which slide along the outside surfaces of the aforementioned light-transmitting tubes and are attached in a freely detachable manner to the supporting bodies.

9. A light irradiating device as defined in claim 4, wherein the driving means comprises a motor.

10. A light irradiating device as defined in claim 4, wherein the moving means comprises a screw shaft.

11. A light irradiating device as defined in claim 4, wherein the cleaning parts comprise brushes, which slide along the outside surfaces of the aforementioned light-transmitting tubes and are attached in a freely detachable manner to the supporting bodies.

* * * * *